United States Patent [19]

Gray

[11] 4,439,429

[45] Mar. 27, 1984

[54] METHOD OF ALLEVIATING SYSTEMIC MYCOTIC INFECTIONS

[75] Inventor: Joseph E. Gray, Norwich, N.Y.

[73] Assignee: Norwich Eaton Pharmaceuticals, Inc., Norwich, N.Y.

[21] Appl. No.: 316,859

[22] Filed: Oct. 30, 1981

[51] Int. Cl.$^3$ .............................................. A61K 31/34
[52] U.S. Cl. .................................................... 424/285
[58] Field of Search ......................................... 424/285

[56] References Cited

PUBLICATIONS

Oleinik et al., Gyogyszereszet, 1975, 19(7), pp. 252–256.

Primary Examiner—Jerome D. Goldberg
Attorney, Agent, or Firm—Anthony J. Franze

[57] ABSTRACT

5-(p-Chlorophenyl)-2-furaldehyde oxime is useful in treating systemic mycotic infections.

1 Claim, No Drawings

METHOD OF ALLEVIATING SYSTEMIC MYCOTIC INFECTIONS

This invention is concerned with the treatment of systemic mycotic infections. More particularly, it is concerned with a method of treating systemic mycotic infections by the administration of 5-(p-chlorophenyl)-2-furaldehyde oxime to a host.

The compound 5-(p-chlorophenyl)-2-furaldehyde oxime has been described in Khim. Geterotsikl. Soedin. 1148 (1972); Chemical Abstracts 78, 43169q (1973).

It has now been discovered that 5-(p-chlorophenyl)-2-furaldehyde oxime, when administered perorally by gavage in water to mice infected with *Torulopsis glabrata* systemic infection, significant activity is elicited. A reduction in viable cell count is noted in both spleen and heart tissue at doses ranging from 35 to 100 mg/kg. Suitable pharmaceutical compositions for administration of 5-(p-chlorophenyl)-2-furaldehyde oxime comprise those commonly employed dosage formulations such as tablets, solutions, suspensions and capsules using commonly employed excipients and adjuvants, such forms containing from 10 to 500 mg of the compound per unit dosage form.

What is claimed is:

1. A method for alleviating systemic mycotic infection caused by the organism *Torulopsis glabrata* which consists in perorally administering to a host in need of said treatment a composition containing an antimycotic effective amount of the compound 5-(p-chlorophenyl)-2-furaldehyde oxime.

* * * * *